(12) United States Patent  (10) Patent No.: US 8,848,182 B2
Amako et al.  (45) Date of Patent: Sep. 30, 2014

(54) OPTICAL DEVICE, ANALYZING APPARATUS AND SPECTROSCOPIC METHOD

(75) Inventors: Jun Amako, Matsumoto (JP); Kohei Yamada, Minowa (JP)

(73) Assignee: Seiko Epson Corporation (JP)

( * ) Notice: Subject to any disclaimer, the term of this patent is extended or adjusted under 35 U.S.C. 154(b) by 722 days.

(21) Appl. No.: 13/095,103

(22) Filed: Apr. 27, 2011

(65) Prior Publication Data

US 2011/0267613 A1  Nov. 3, 2011

(30) Foreign Application Priority Data

Apr. 28, 2010  (JP) .................................. 2010-103035

(51) Int. Cl.
G01J 3/44 (2006.01)
G01N 21/55 (2014.01)
G01N 21/65 (2006.01)

(52) U.S. Cl.
CPC ............ *G01N 21/658* (2013.01); *G01N 21/554* (2013.01)
USPC ........................................................ 356/301

(58) Field of Classification Search
USPC ........................................................ 356/301
See application file for complete search history.

(56) References Cited

U.S. PATENT DOCUMENTS

| 7,397,559 B1 * | 7/2008 | Bratkovski ..................... 356/301 |
| 7,599,066 B2 | 10/2009 | Fukuda |
| 2001/0002315 A1 * | 5/2001 | Schultz et al. ................. 436/172 |
| 2006/0119853 A1 | 6/2006 | Baumberg et al. |
| 2009/0195879 A1 * | 8/2009 | Dal Negro et al. ............ 359/586 |
| 2009/0273779 A1 | 11/2009 | Baumberg et al. |
| 2010/0321684 A1 * | 12/2010 | Bratkovski et al. ........... 356/301 |
| 2011/0053794 A1 * | 3/2011 | Zhang ................................ 506/9 |

FOREIGN PATENT DOCUMENTS

| JP | 2000-356587 | 12/2000 |
| JP | 2006-093055 A | 4/2006 |
| JP | 2007-010648 | 1/2007 |
| JP | 2008-519254 A | 6/2008 |
| JP | 2009-250951 | 10/2009 |

OTHER PUBLICATIONS

European Extended Search Report for Application No. 11164070.2 dated Aug. 29, 2011 (11 pages).
Ming-Wang Shao, et al. "Ag-modified silicon nanowires substrate for ultrasensitive surface-enhanced raman spectroscopy" American Institute of Physics, Applied Physics Letters 93, 233118 (2008) (pp. 233118-1 through 233118-3).

(Continued)

*Primary Examiner* — Kara E Geisel
(74) *Attorney, Agent, or Firm* — Harness, Dickey & Pierce, P.L.C.

(57) ABSTRACT

An optical device includes a first projection group in which electrically conductive projections are arranged at a first period along a direction parallel to a virtual plane. When light traveling in a direction inclined with respect to a vertical line directed to the virtual plane is incident on the first projection group, surface plasmon resonance is generated at a first resonance peak wavelength and a second resonance peak wavelength. A first resonance peak wavelength band including the first resonance peak wavelength includes an excitation wavelength in surface-enhanced Raman scattering. A second resonance peak wavelength band including the second resonance peak wavelength includes a Raman scattering wavelength in the surface-enhanced Raman scattering.

19 Claims, 10 Drawing Sheets

(56) References Cited

OTHER PUBLICATIONS

Tadashi Takemori, et al., "Optical Response of a Sphere Coupled to a Metal Substrate", Journal of the Physical Society of Japan, vol. 56, No. 4, Apr. 1987, (pp. 1587-1602).

Inoue, Masahiro and Ohtaka, Kazuo, "Surface Enhanced Raman Scattering by Metal Spheres. I. Cluster Effect", Journal of the Physical Society of Japan, vol. 52, Nov. 11, 1983, pp. 3853-3864.

Li, Lifeng and Haggans, Charles W., "Convergence of the coupled-wave method for metallic lamellar diffraction gratings", J. Opt. Soc. Am. A/vol. 10, No. 6/Jun. 1993, pp. 1184-1189.

* cited by examiner

OPTICAL DEVICE, ANALYZING APPARATUS AND SPECTROSCOPIC METHOD

This application claims priority to Japanese Patent Application No. 2010-103035 filed Apr. 28, 2010 which is hereby expressly incorporated by reference herein in its entirety.

BACKGROUND

1. Technical Field

The present invention relates to an optical device, an analyzing apparatus and a spectroscopic method.

2. Related Art

In recent years, the demand for a sensor used for medical diagnosis, food inspection or the like has increased, and the development of a highly sensitive small sensor has been requested. In order to meet such a request, various types of sensors including one using an electrochemical method have been studied. Among these, interest in a sensor using surface plasmon resonance has increased because the sensor can be integrated, manufactured at low cost, and used in any measurement environment.

For example, JP-A-2000-356587 discloses a method in which sensor sensitivity is improved by using localized surface plasmon resonance caused by a substrate having fine metal particles fixed on the surface thereof.

JP-A-2007-10648 and JP-A-2009-250951 are other examples of the related art.

When the intensity of Raman scattering is enhanced by using an electric field that is enhanced by surface plasmon resonance, and the target sensing sensitivity is improved, the degree of electric field enhancement is determined by the product of the degree of electric field enhancement at an excitation wavelength and the degree of electric field enhancement at a Raman scattering wavelength. Thus, in order to improve the sensing sensitivity, it is necessary to increase both the degree of electric field enhancement at the excitation wavelength and the degree of electric field enhancement at the Raman scattering wavelength.

For example, in the method of JP-A-2000-356587, since it is difficult to equalize the sizes of the fine metal particles and their arrangements, variations occur in the resonant wavelength, and the width of an absorbance spectrum becomes broad. Further, only one resonant peak occurs. Thus, for example, when sensing a rare target, it is difficult to obtain a sufficient degree of electric field enhancement in both the excitation wavelength and the Raman scattering wavelength.

Incidentally, JP-A-2007-10648 discloses a localized plasmon resonance sensor having a resonant peak shifted to a longer wavelength side and a resonant peak shifted to a shorter wavelength side. JP-A-2009-250951 discloses an electric field enhancement device in which a micro resonator is constructed of plural resonant areas in order to enable resonance to occur at plural wavelengths.

SUMMARY

An advantage of some aspects of the invention is to provide an optical device, an analyzing apparatus and a spectroscopic method, in which the degree of electric field enhancement at an excitation wavelength and at a Raman scattering wavelength can be improved.

One aspect of the invention relates to an optical device including: a first projection group in which electrically conductive projections are arranged at a first period along a direction parallel to a virtual plane. When light traveling in a direction inclined with respect to a vertical line directed to the virtual plane is incident on the first projection group arranged at the first period, surface plasmon resonance is generated at a first resonance peak wavelength and a second resonance peak wavelength. A first resonance peak wavelength band including the first resonance peak wavelength includes an excitation wavelength $\lambda 1$ in surface-enhanced Raman scattering, and a second resonance peak wavelength band including the second resonance peak wavelength includes a Raman scattering wavelength $\lambda 2$ in the surface-enhanced Raman scattering.

According to this aspect of the invention, the electrically conductive projections of the first projection group are arranged at the first period along the direction parallel to the virtual plane. The light traveling in the direction inclined with respect to the vertical line directed to the virtual plane is incident on the first projection group arranged at the first period. The surface plasmon resonance is generated at the first resonance peak wavelength and the second resonance peak wavelength by the incident light. At this time, the first period and the light incident angle are set so that the first resonance peak wavelength band including the first resonance peak wavelength includes the excitation wavelength $\lambda 1$ in the surface-enhanced Raman scattering, and the second resonance peak wavelength band including the second resonance peak wavelength includes the Raman scattering wavelength $\lambda 2$ in the surface-enhanced Raman scattering. As a result, the degree of electric field enhancement at the excitation wavelength and at the Raman scattering wavelength can be improved.

This aspect of the invention may be configured such that the Raman scattering wavelength $\lambda 2$ is longer than the excitation wavelength $\lambda 1$.

By doing this, a target can be detected by using the Raman scattering wavelength $\lambda 2$ that is longer than the excitation wavelength $\lambda 1$ in the Raman scattering light.

This aspect of the invention may be configured such that a linearly polarized light in which a component of a polarization direction parallel to the virtual plane is parallel to an arrangement direction of the first projection group is incident as the incident light.

By doing this, the polarized light in which the component of the polarization direction parallel to the virtual plane is parallel to the arrangement direction of the first projection group can be made incident on the optical device. As a result, propagating surface plasmon can be excited.

This aspect of the invention may be configured such that a second projection group of electric conductors is provided on a top surface of the first projection group, and the second projection group is arranged at a second period shorter than the first period along the direction parallel to the virtual plane.

By doing this, the second projection group can be arranged on the top surface of the first projection group at the second period along the direction parallel to the virtual plane. As a result, localized surface plasmon can be excited in the second projection group.

This aspect of the invention may be configured such that a third projection group of electric conductors is provided on a surface on which the first projection group is arranged and which is located between the adjacent projections of the first projection group, and the third projection group is arranged at a third period shorter than the first period along the direction parallel to the virtual plane.

By doing this, the third projection group can be arranged on the surface on which the first projection group is arranged and which is located between the adjacent projections of the first projection group and at the third period along the direction parallel to the virtual plane. As a result, the localized surface plasmon can be excited in the third projection group.

Another aspect of the invention relates to an analyzing apparatus including: a light source, the optical device as described above, a first optical system that causes incident light of the wavelength λ1 from the light source to be inclined with respect to the vertical line directed to the virtual plane of the optical device and causes the light to be incident on the diffraction grating, a second optical system that extracts Raman scattering light from the light scattered or reflected by the electrically conductive grating of the optical device, and a detector to detect the Raman scattering light received through the second optical system.

This aspect of the invention may be configured such that the first optical system shifts the incident light from an optical axis of the first optical system and causes the light to be incident, and the light is inclined with respect to the vertical line directed to the virtual plane and is incident on the electrically conductive grating.

This aspect of the invention may be configured such that a support part is provided which causes the vertical line directed to the virtual plane of the optical device to be inclined with respect to the optical axis of the first optical system and supports the optical device, the first optical system causes the incident light to coincide with the optical axis of the first optical system and to be incident, and the incident light is inclined with respect to the vertical line directed to the virtual plane and is incident on the electrically conductive grating.

Still another aspect of the invention relates to a spectroscopic method including: preparing a first projection group in which electrically conductive projections are arranged at a first period along a direction parallel to a virtual plane, causing light traveling in a direction inclined with respect to a vertical line directed to the virtual plane to be incident on the first projection group arranged at the first period, generating surface plasmon resonance at a first resonance peak wavelength and a second resonance peak wavelength, causing a first resonance peak wavelength band including the first resonance peak wavelength to include an excitation wavelength λ1 in surface-enhanced Raman scattering, and causing a second resonance peak wavelength band including the second resonance peak wavelength to include a Raman scattering wavelength λ2 in the surface-enhanced Raman scattering.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the invention will be described in detail. Incidentally, the embodiments described below do not limit the scope of the invention recited in the claims, and all components described in the embodiments are not necessarily indispensable to the invention.

1. Comparative Example

Figure 1:
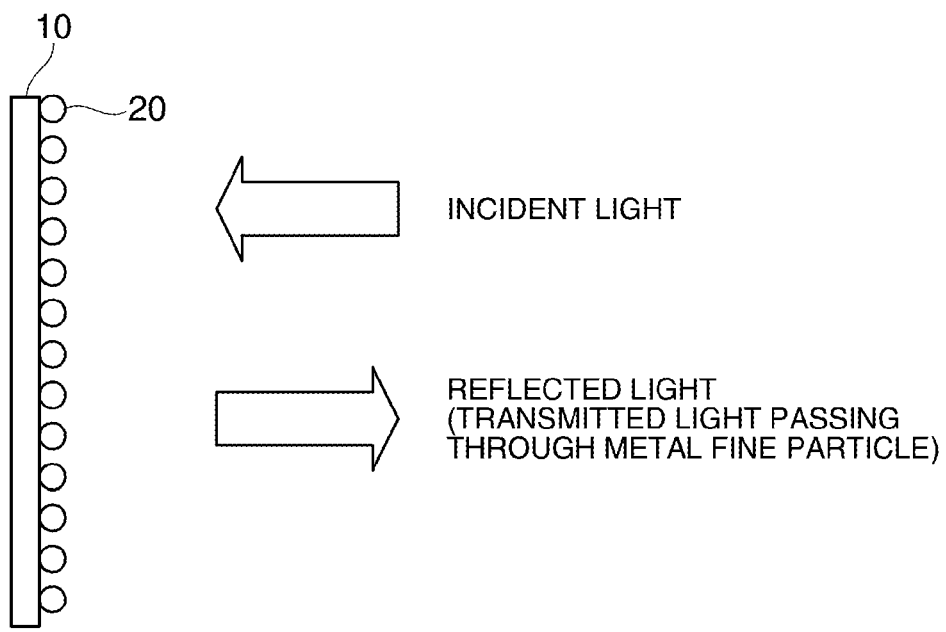
FIG. 1 is an explanatory view of a comparative example of an embodiment.
Figure 2:
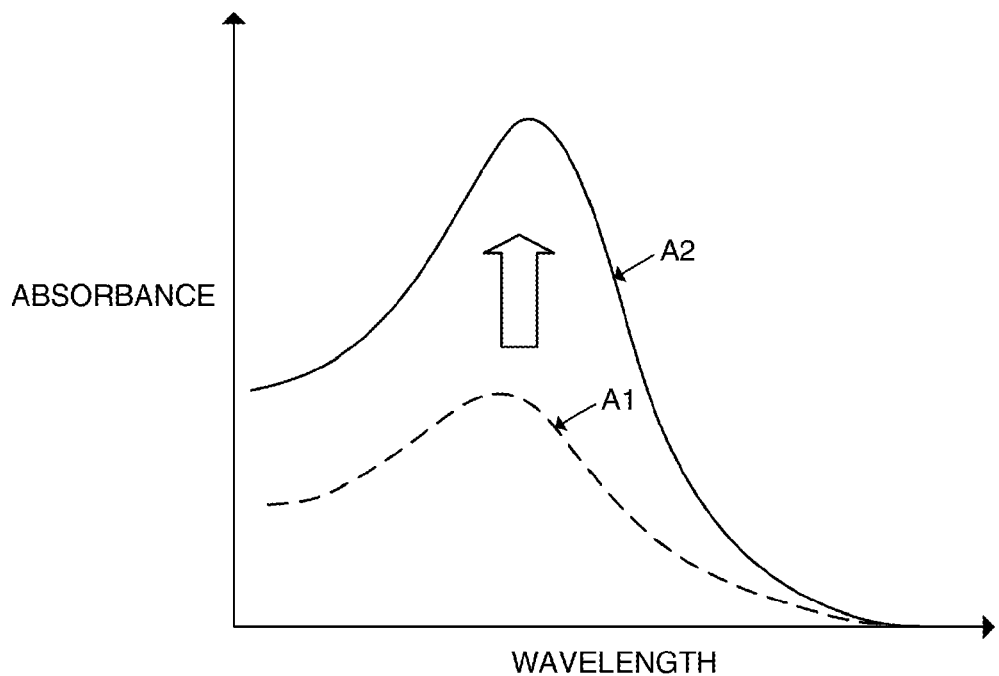
FIG. 2 is an explanatory view of the comparative example of the embodiment.
Figure 3:
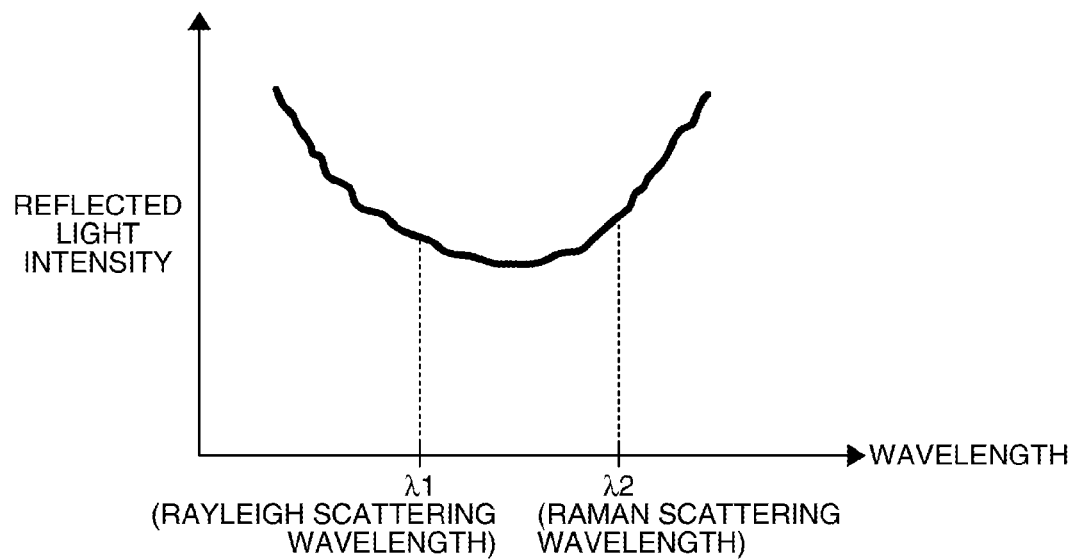
FIG. 3 is an explanatory view of the comparative example of the embodiment.

As a comparative example of an embodiment, a case where localized surface plasmon resonance caused by fine metal particles is used in surface-enhanced Raman scattering spectroscopy will be described with reference to FIG. 1 to FIG. 3. First, the localized surface plasmon resonance caused by the fine metal particles will be described with reference to FIG. 1 and FIG. 2.

As described above, there is a growing interest in a sensor using surface plasmon resonance (SPR) as a highly sensitive small sensor used for medical diagnosis or the like. In this sensor, surface plasmon (SP) is excited on a metal surface by excitation light, and a target attached to the metal surface is sensed by using a change of absorbance due to the surface plasmon resonance. Here, the surface plasmon resonance is an oscillation mode of an electron compression wave which is coupled to light according to a boundary condition intrinsic to an interface.

As a method of exciting the surface plasmon, a method of using a surface concave-convex grating or a prism is known. For example, as a sensor using the surface plasmon resonance, there is a method of using a total reflection prism. In this method, a metal film is formed on the surface of the total reflection prism, and a target is brought into contact with the metal film. When excitation light is incident on the total reflection prism, propagating surface plasmon is excited on the interface between the air and the metal film, and the presence or absence of adsorption of the target is detected by change of absorbance caused by the propagating surface plasmon. As a method of adsorbing the target, an antigen-antibody reaction or the like is used.

As another method of exciting the surface plasmon, there is a method of exciting localized surface plasmon (LSP) by fine metal particles. In the localized surface plasmon, the excited surface plasmon is localized on a fine structure formed on a substrate surface, and a remarkably enhanced electric field is induced by the localized surface plasmon. A sensor using localized surface plasmon resonance (LSPR) and using fine metal particles or a metal nano-structure is proposed in order to improve sensor sensitivity by using the enhanced electric field as stated above.

For example, as such a sensor, there is a method as described in JP-A-2000-356587. In this method, as shown in FIG. 1, fine metal particles 20 are fixed on a surface of a transparent substrate 10, incident light is emitted to the transparent substrate 10, and the absorbance of the reflected light passing through the fine metal particles 20 is measured. As shown in FIG. 2, when a target is attached to the fine metal particles 20, an absorbance spectrum indicated by A1 is changed to an absorbance spectrum indicated by A2. In the method of JP-A-2000-356587, the change of a medium in the vicinity of the fine metal particles is detected by the change of the absorbance, and the adsorption or deposition of the target is detected.

However, in this method, it is difficult to uniformly form the size and shape of the fine metal particles and to regularly arrange the fine metal particles. When the size and arrangement of the fine metal particles can not be controlled, variations occur in the absorption caused by the plasmon resonance and the resonant wavelength. Thus, as shown in FIG. 2, the width of the absorbance spectrum becomes broad, and the peak intensity decreases. When the peak intensity decreases, a signal change for detecting the change of the medium in the vicinity of the fine metal particles becomes small, and there arises a limit in improving sensor sensitivity. Thus, when attempting to specify a material from an absorbance spectrum, the sensitivity of the sensor becomes insufficient.

As a method of improving the sensitivity of the sensor, a method of applying the foregoing sensor to surface-enhanced Raman scattering (SERS) is conceivable. In this method, Raman scattering light is enhanced by the surface plasmon resonance so that the sensitivity of the Raman spectroscopy is improved.

However, in this method, since the sensor sensitivity is determined (following expression (1)) by the degree of electric field enhancement at the excitation wavelength ($\lambda 1$ shown in FIG. 4A) and the Raman scattering wavelength ($\lambda 2$), it is necessary to enhance the degree of electric field enhancement at both wavelengths.

For example, in the surface-enhanced Raman scattering sensor of the related art, since only one resonant peak is used, the wavelength of the resonant peak must be adjusted to one of the excitation wavelength and the Raman scattering wavelength. In this case, since only an electric field enhancement effect in the scattering process of either one of them is used, a high electric field enhancement effect can not be expected.

Next, it will be assumed that the sensor of JP-A-2000-356587 is applied to the surface-enhanced Raman scattering. In this case, as described above in FIG. 2, since only one broad surface plasmon resonance peak exists, it is necessary to set the position of the resonant peak at a suitable position with respect to the excitation wavelength and the Raman scattering wavelength. That is, the resonance peak wavelength exerts a large influence on the degree of enhancement of localized electric field. Specifically, as shown in FIG. 3, a relatively broad resonant peak is obtained for Raman shift. Thus, when the resonance peak wavelength is set between the excitation wavelength and the Raman scattering wavelength, the electric field enhancement effect can be expected for both the excitation process and the Raman scattering process. However, since the resonant peak is broad, the intensity of resonance becomes low in each of the processes, and the enhancement degree of the entire process may be insufficient.

2. Method of the Embodiment

In this embodiment, incident light is obliquely incident on a metal grating as an example of an electrically conductive grating to generate two resonant peaks, and the two resonant peaks are set to the excitation wavelength and the Raman scattering wavelength, so that the sensor sensitivity is improved. In the following, the method of the embodiment will be described. First, a Raman scattering spectroscopic method used in this embodiment will be described.

Figure 4A:
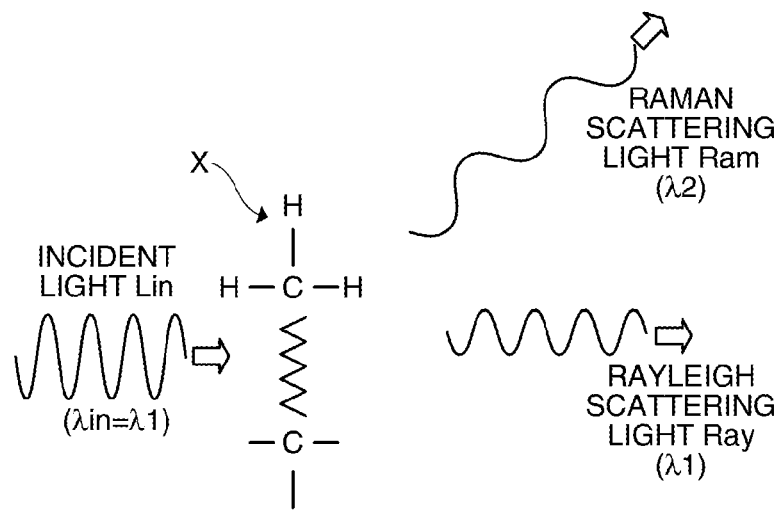
FIG. 4A is an explanatory view of the principle of a Raman scattering spectroscopic method.

FIG. 4A is an explanatory view of the principle of the Raman scattering spectroscopic method. As shown in FIG. 4A, when light Lin of a single wavelength is emitted to a target molecule X (target), Raman scattering light Ram of a wavelength $\lambda 2$ different from a wavelength $\lambda$in of the incident light Lin is generated in the scattering light. The energy difference between the Raman scattering light Ram and the incident light Lin corresponds to the energy of oscillation level, rotational level or electron level of the target molecule X. Since the target molecule X has an intrinsic oscillation energy according to its structure, the target molecule X can be specified by using the light Lin of the single wavelength.

For example, when the oscillation energy of the incident light Lin is V1, the oscillation energy of the target molecule X is V2, and the oscillation energy of the Raman scattering light Ram is V3, V3=V1−V2 is established. That is, since V3 becomes the oscillation energy corresponding to V2, the target molecule X can be specified by measuring the wavelength $\lambda 2$ of the Raman scattering light Ram.

Incidentally, most of the incident light Lin has the same energy as that before collision even after the incident light collides with the target molecule X. The elastic scattering light is called the Rayleigh scattering light Ray. For example, when the oscillation energy of the Rayleigh scattering light Ray is V4, V4=V1 is established. That is, the wavelength $\lambda 1$ of the Rayleigh scattering light Ray is $\lambda 1 = \lambda$in.

Figure 4B:
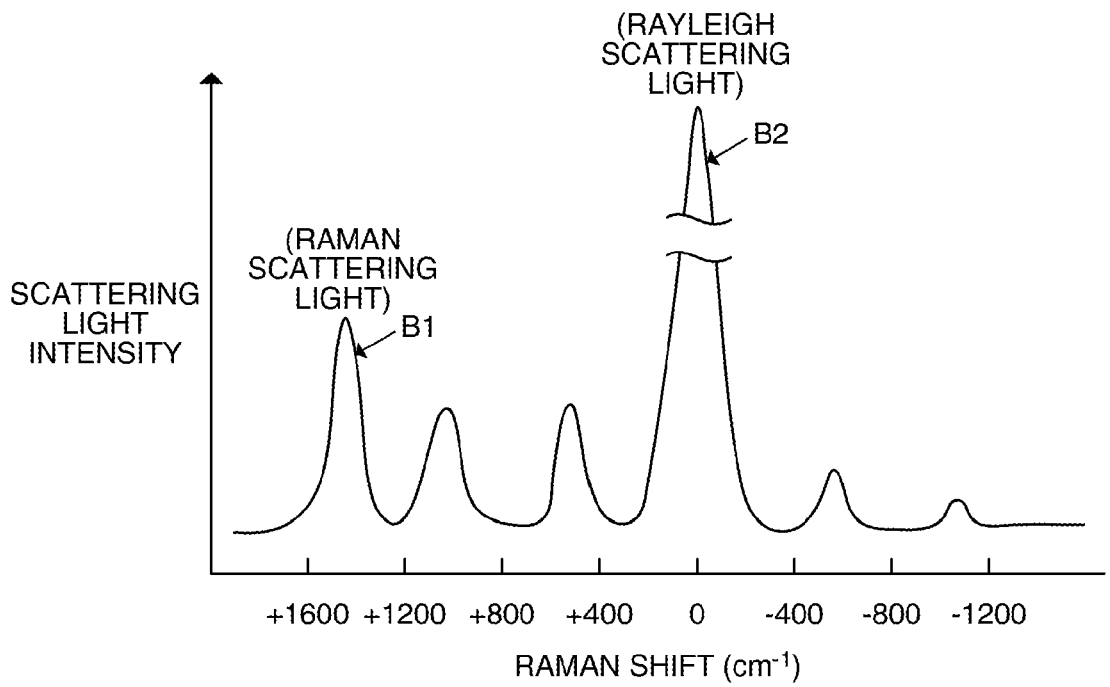
FIG. 4B shows an example of Raman spectrum acquired by Raman scattering spectroscopy.

FIG. 4B shows an example of a Raman spectrum (the relation between Raman shift and Raman scattering intensity) acquired by the Raman scattering spectroscopy. The horizontal axis of the graph shown in FIG. 4B indicates the Raman shift. The Raman shift is a difference between the wave number (frequency) of the Raman scattering light Ram and the wave number of the incident light Lin, and is a value intrinsic to the molecule bonding state of the target molecule X.

As shown in FIG. 4B, when the scattering intensity (spectrum peak) of the Raman scattering light Ram indicated by B1 is compared with the scattering intensity of the Rayleigh scattering light Ray indicated by B2, it is understood that the Raman scattering light Ram is weaker. As stated above, the Raman scattering spectroscopic method is excellent in discrimination capacity of the target molecule X, the sensitivity of sensing the target molecule X is low. Thus, in this embodiment, the sensitivity of the sensor is raised by using the spectroscopic method using the surface-enhanced Raman scattering.

In order to realize the high sensitivity surface plasmon resonance sensor using the surface-enhanced Raman scattering, it is desirable that the degree of enhancement of localized electric field (hereinafter suitably abbreviated to enhancement degree) is as high as possible. The enhancement degree $\alpha$ is expressed by the following expression (1) (M. Inoue, K. Ohtaka, J. Phys. Soc. Jpn., 52, 3853 (1983)). Here, $\alpha$ray denotes the enhancement degree at the excitation wavelength (equal to the Rayleigh scattering wavelength), and $\alpha$ram denotes the enhancement degree at the Raman scattering wavelength.

$$\alpha = \alpha_{ray} \times \alpha_{ram} \quad (1)$$

Figure 5:
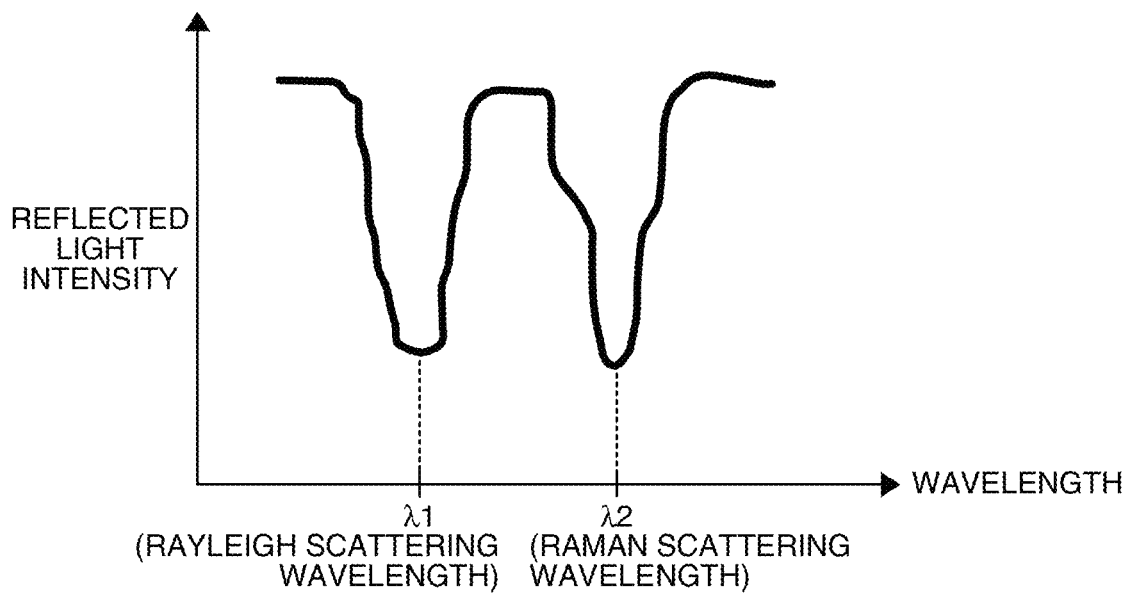
FIG. 5 is an explanatory view of a method of the embodiment.

From the above expression (1), in order to raise the enhancement degree in the surface-enhanced Raman scattering process, it is necessary to simultaneously raise both the enhancement degree in the excitation process and the enhancement degree in the Raman scattering process. For that purpose, in this embodiment, as shown in FIG. 5, two high resonant peaks are generated only in the vicinity of the excitation wavelength and the Raman scattering wavelength. As a result, the enhancement effect of the localized electric field can be remarkably raised by the synergy effect of both the scattering processes.

3. Structural Example

A structural example of the embodiment in which two resonant peaks are generated in the vicinity of an excitation wavelength and a Raman scattering wavelength will be described with reference to FIG. 6 to FIG. 9. Incidentally, in the following, in order to cause the sizes of respective components to become such that they can be recognized in the drawings, the sizes and ratios of the respective components are suitably made different from actual ones.

Figure 6:
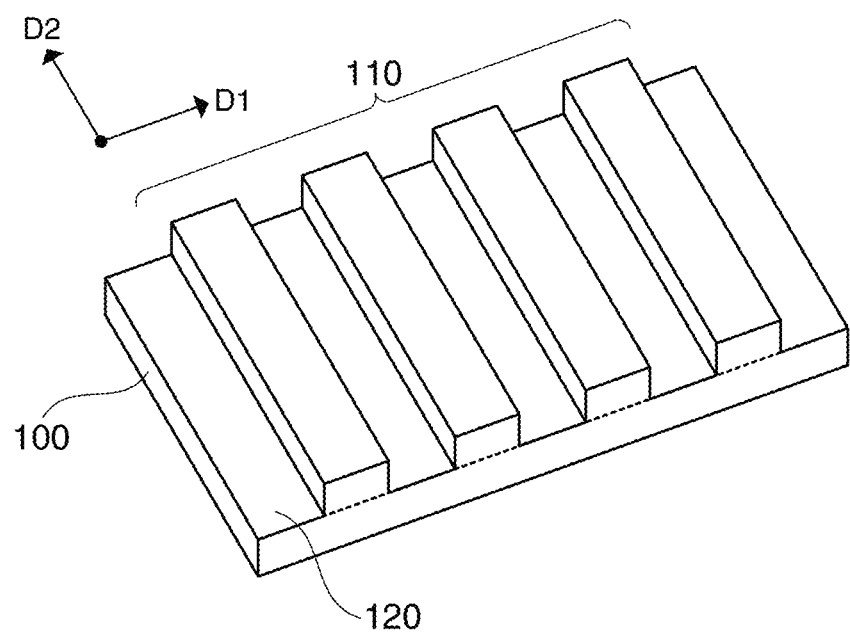
FIG. 6 is a perspective view of a structural example of a sensor chip of the embodiment.

FIG. 6 is a perspective view of a structural example of a sensor chip (optical device, electrically conductive grating) of the embodiment. The sensor chip is for detecting a target (target material, target molecule) by using the surface plasmon resonance and the surface-enhanced Raman scattering, and includes a base member 100 (substrate) and a first projection group 110. The sensor chip is a metal grating having one-dimensional periodicity.

Incidentally, in the following, although a description will be made of the case where the sensor chip is a metal grating made of metal, the embodiment is not limited to this case. That is, the sensor chip may be a grating made of any electric conductor, and may be, for example, a grating made of a semiconductor material (for example, polysilicon).

Specifically, the base member 100 includes a metal (electric conductor in a broad sense), such as Ag (silver) or Au (gold), and is formed into, for example, a square or circular flat plate shape. The first projection group 110 is periodically arranged in a first direction D1 along a plane (surface in a broad sense) of the base member 100, and is made of, for example, the same metal as the base member 100. Here, the plane of the base member 100 is, for example, a surface 120 of the base member 100 at the side where the first projection group 110 is formed.

More specifically, in each projection of the first projection group 110, the sectional shape of the projection in the arrangement direction D1 is formed in a convex shape from the surface 120 of the base member 100. The convex shape is a rectangle, a trapezoid, an arc, or the like. For example, as shown in FIG. 6, the first projection group 110 is formed in a stripe shape parallel to a second direction D2 perpendicular to the direction D1 when the base member 100 is seen in a plan view.

Figure 7:
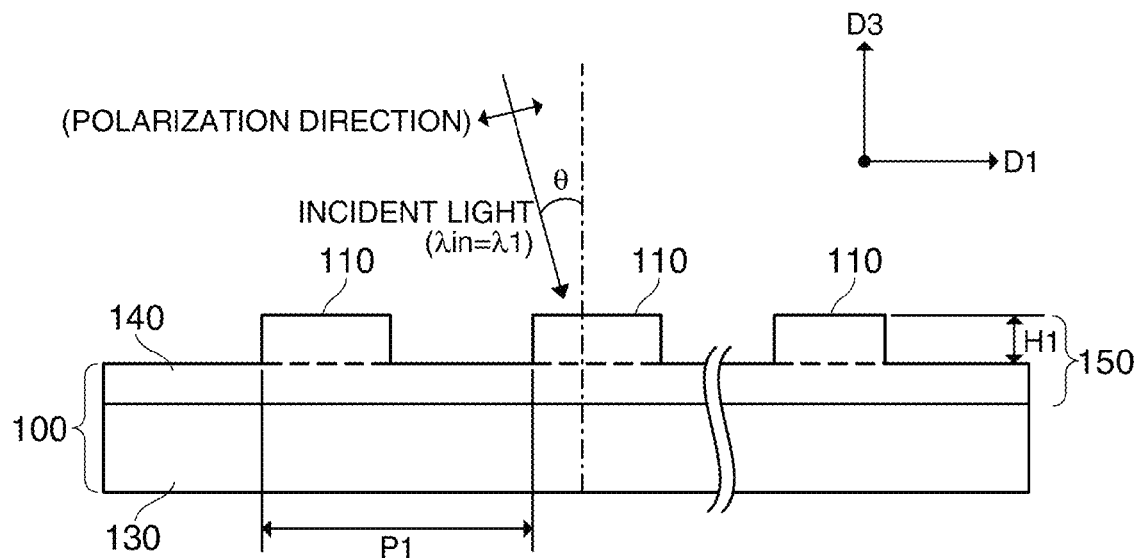
FIG. 7 is a sectional view of the sensor chip of the embodiment.

FIG. 7 is a sectional view of the sensor chip of the embodiment. The section of the sectional view is a surface perpendicular to the plane of the base member 100 and is a surface parallel to the arrangement direction D1 of the first projection group 110. As shown in FIG. 7, a normal direction of the plane of the base member 100 is a direction D3.

The base member 100 is such that a metal thin film 140 is formed on a glass substrate 130. For example, the thickness of the metal thin film 140 is 150 nm or more. The sectional shape of the first projection group 110 is rectangular (approximately rectangular), and the projection of height H1 is arranged at a first period P1 along the direction D1. A metal grating 150 (periodic metal concave-convex structure) is formed of the metal thin film 140 and the first projection group 110. It is desirable that the period P1 is set within a range of 100 to 1000 nm, and the height H1 is set within a range of 10 to 100 nm.

Incident light including linearly polarized light is incident on the sensor chip. The polarization direction (polarization orientation) of the linearly polarized light is a direction parallel to a surface parallel to the direction D1 and D3. The incident light is obliquely incident on the metal grating 150 formed of the metal thin film 140 and the first projection group 110. Specifically, when an inclined angle is θ, θ>0 is established, and the incident light is made incident so that in the section shown in FIG. 7, an angle between the incident direction and a direction opposite to the direction D3 (angle relative to the vertical line directed to the plane of the base member 100) becomes θ.

In the above, although the linearly polarized light is parallel to the surface parallel to the direction D1 and D3, in this embodiment, the linearly polarized light may not be parallel to the surface, but includes a polarization component parallel to the surface. Further, in the above, although the base member 100 is such that the metal thin film 140 is formed on the glass substrate 130, the embodiment is not limited to this. For example, the base member 100 of the embodiment may be such that a metal film is formed on a quartz substrate or a sapphire substrate. Further, a flat plate made of a metal may be used as the base member 100.

Figure 8:
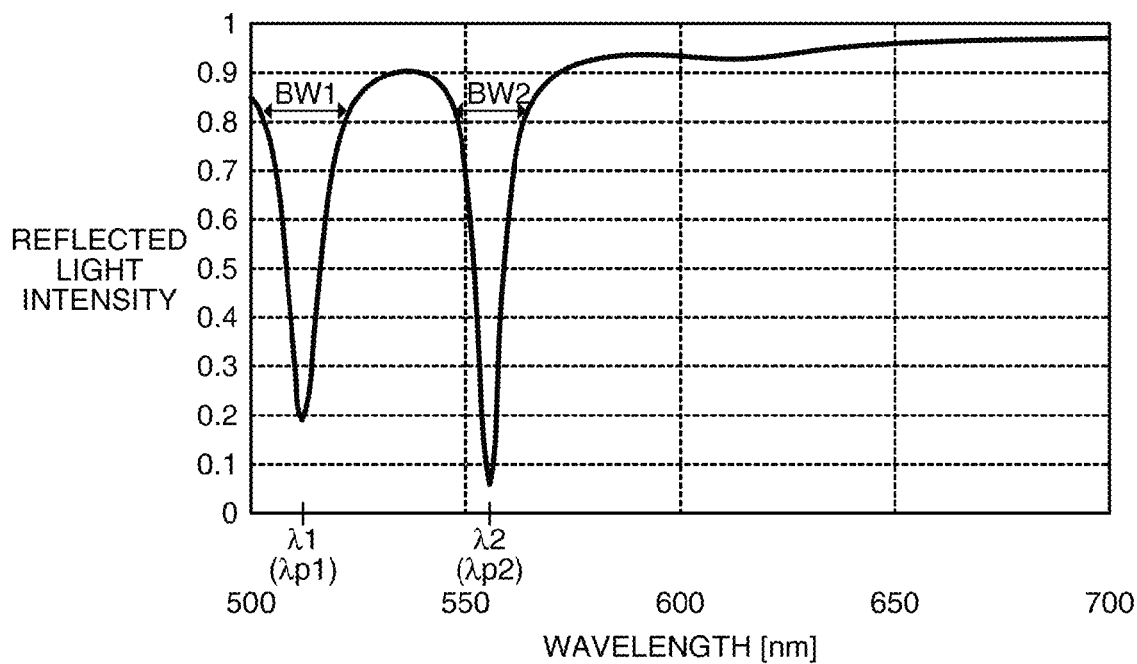
FIG. 8 is a view of a characteristic example of reflected light intensity of the sensor chip.

FIG. 8 shows a characteristic example of reflected light intensity of the sensor chip. FIG. 8 shows the characteristic example in the case where the metal grating is made of Ag, the incident angle θ of the light relative to the metal grating is 3 degrees, the polarization direction of the light is perpendicular to the groove direction D2 of the metal grating, the section of the projection is rectangular (approximately rectangular), the period P1 is 500 nm, and the height H1 is 20 nm. Incidentally, the horizontal axis indicates the wavelength of the reflected light, and the vertical axis indicates the reflected light intensity (ratio to the incident light intensity).

As shown in FIG. 8, in the metal grating of the embodiment, there are two resonant peaks of the surface plasmon polariton (SPP). For example, one resonant peak is located near a wavelength of 515 nm, and the other resonant peak is located near a wavelength of 555 nm. When the two resonant peaks are adjusted to be approximately equal to (or made to coincide) the excitation wavelength and the Raman scattering wavelength, a high enhanced Raman scattering effect can be expected. For example, when an argon laser of a wavelength of 515 nm is used for the excitation wavelength, the Raman scattering light (Raman shift of 1200 to 1600 $cm^{-1}$) in the vicinity of the wavelength of 555 nm can be significantly enhanced.

Incidentally, as the target to which the embodiment is applied, for example, rare molecules of drug, alcohol or residual agrichemical, and pathogens such as a virus are conceivable.

4. Setting Method of Resonance Peak Wavelength

A setting method of two resonance peak wavelengths will be described with reference to FIG. 9. First, the function of the sensor chip of this embodiment will be described.

When light is incident on the grating surface of the sensor chip, surface plasmon is generated by the convex-concave structure of the grating. In this embodiment, the light is made obliquely incident on the grating surface of the sensor chip. The incident angle θ is several degrees (for example, 10 degrees or less). When the polarization direction of the incident light is made perpendicular to the groove direction of the grating, oscillation of an electromagnetic wave is excited by oscillation of free electrons in the metal grating. Since the oscillation of the electromagnetic wave influences the oscillation of the free electrons, a surface plasmon polariton as a system in which both the oscillation are coupled is formed.

The surface plasmon polariton propagates along the surface of the sensor chip. Specifically, the surface plasmon polariton propagates along the interface between the air and the metal grating, and excites an intense localized electric field in the vicinity of the metal grating. The coupling of the surface plasmon polariton is sensitive to the wavelength of the light, and the coupling efficiency is high. For example, when one to several targets are adsorbed to the surface of the grating, surface-enhanced Raman scattering is generated. In this way, the enhanced electric field is excited through the surface plasmon polariton from the incident light in the air propagation mode, and the surface-enhanced Raman scattering is generated by the interaction between the enhanced electric field and the target. In this embodiment, the width of the reflected light intensity spectrum is narrow, and the two resonant peaks can be made sharp. As a result, the sensor sensibility is improved, and the sensor chip can be realized in which a target material can be specified from the surface-enhanced Raman scattering spectrum.

Figure 9:
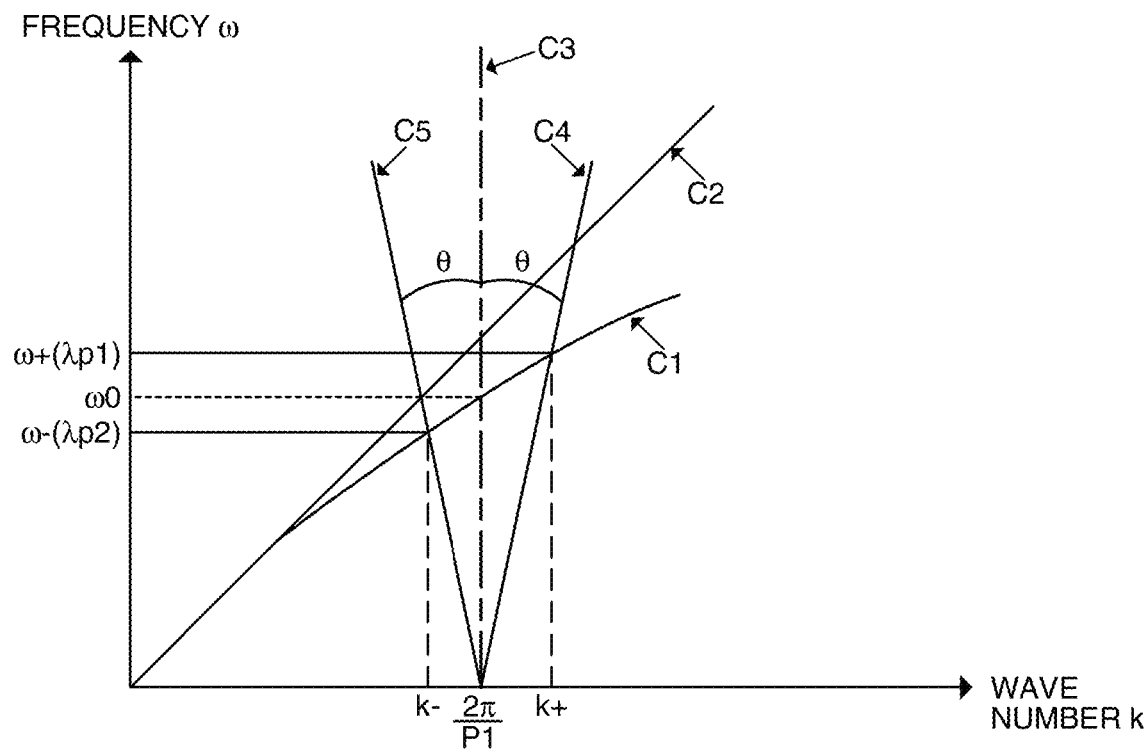
FIG. 9 is an explanatory view of a setting method of two resonance peak wavelengths.

FIG. 9 is an explanatory view of an excitation condition of the surface plasmon polariton. In FIG. 9, C1 represents a dispersion curve of the surface plasmon polariton (for example, dispersion curve on a boundary surface between the air and Au), and C2 represents a light line. In FIG. 9, the period of the metal grating is P1, and the wave number $2\pi/P1$ of a grating vector in this case is indicated on the horizontal axis.

First, the relation between the metal grating and the excitation condition will be described. When the wave number of the incident light is ki, and the incident angle is θ, the wave number of a primary evanescent wave in the arrangement direction (direction D1 or −D1 shown in FIG. 7) of the metal grating is $2\pi/P1 \pm ki \cdot \sin\theta$. The surface plasmon polariton is excited when the wave number $2\pi/P1 \pm ki \cdot \sin\theta$ of the evanescent wave coincides with the wave number of the surface plasmon. That is, the excitation condition of the surface plasmon polariton is represented by the intersection point between the straight line representing the generation condition of the evanescent wave and the dispersion curve of the surface plasmon polariton.

In FIG. 9, C3 represents a straight line expressing a generation condition of an evanescent wave when light is vertically (θ=0) incident on the metal grating. As indicated by C3, the wave number of the evanescent wave in this case is expressed by $2\pi/P1$. The straight line C3 is a line extended upward from the position of the wave number of the grating vector, and intersects with the dispersion curve C1 of the surface plasmon polariton. At this time, the number of intersection points is one, and only one resonant peak appears at a frequency ω0 (angular frequency).

C4 and C5 represent straight lines expressing the generation condition of the evanescent wave in the embodiment. As in this embodiment, when the light is incident on the metal grating at an angle θ (θ>0), the wave number of the evanescent wave is expressed by $2\pi/P1 \pm ki \cdot \sin\theta$. The straight line C4 corresponds to $2\pi/P1 + ki \cdot \sin\theta$, and the straight line C5 corresponds to $2\pi/P1 - ki \cdot \sin\theta$. These straight lines C4 and C5 are lines extended obliquely upward at the angle θ from the position of the wave number of the grating vector, and intersect with the dispersion curve C1 of the surface plasmon polariton at two points. Accordingly, two resonant peaks appear at frequencies ω+ and ω− (corresponding to wavelengths λp1 and λp2).

In this embodiment, the two resonance peak wavelengths λp1 and λp2 are set by using the excitation condition of the surface plasmon polariton, and the two resonance peak wavelengths ***are used for the surface-enhanced Raman scattering. Specifically, first, the dispersion curve C1 is obtained by RCWA (Rigorous Coupled Wave Analysis) (L. Li and C. W. Haggans, J. Opt. Soc. Am., A10, 1184-1189 (1993)). The dispersion curve C1 is a curve intrinsic to the kind of metal, the kind of a medium, and the sectional shape of the metal grating. Next, the desired grating period P1 and the incident angle θ are determined according to the Raman shift of the target. That is, the first resonance peak wavelength λp1 is set in the vicinity of the excitation wavelength (Rayleigh scattering wavelength), and the second resonance peak wavelength λp2 (λp2>λp1) is set in the vicinity of the Raman scattering wavelength. Then, the grating period P1 and the incident angle θ are set so that the straight line C4 passes through an intersection point between the dispersion curve C1 and ω=ω+ (λ=λp1), and the straight line C5 passes through the intersection point between the dispersion curve C1 and ω=ω− (λ=λp2).

In this way, the raw material of the metal grating, the shape, the height H1, the grating period P1 and the light incident angle θ are set, so that the wavelengths λp1 and λp2 of the two resonant peaks can be set to desired values.

In the comparative example as mentioned above, when the surface plasmon resonance has only one broad resonant peak, there is a problem that it is difficult to obtain a sufficient electric field enhancement effect in the entire process of the surface-enhanced Raman scattering.

As shown in FIG. 7, the optical device of this embodiment includes the first projection group 110 in which the electrically conductive projections are arranged at the first period P1 (P1<λ1) along the direction D1 parallel to the plane (virtual plane in a broad sense) of the base member 100. The light (wavelength λ1, incident angle θ) traveling in the direction inclined with respect to the vertical line directed to the plane of the base member 100 is incident on the first projection group 110 arranged at the first period P1. Due to this incident light, as shown in FIG. 9, the surface plasmon resonance is generated at the first resonance peak wavelength λp1 and the second resonance peak wavelength λp2. At this time, as shown in FIG. 8, a first resonance peak wavelength band BW1 including the first resonance peak wavelength λp1 includes the excitation wavelength λ1 in the surface-enhanced Raman scattering. A second resonance peak wavelength band BW2 including the second resonance peak wavelength λp2 includes the Raman scattering wavelength λ2 in the surface-enhanced Raman scattering.

Here, the width of the band BW1, BW2 is the bandwidth at a specified reflected light intensity, and is, for example, half-width of the peak. Incidentally, in FIG. 8, although λ1=λp1 and λ2=λp2 are assumed, in this embodiment, λ1 may be different from λp1, and λ2 may be different from λp2. Also, the virtual plane is the reference plane for the arrangement direction of the first projection group 110 and the incident angle of the incident light, and is, for example, a surface parallel to the plane (for example, the surface 120 of the base member 100) of the base member 100.

According to the embodiment, the degree of electric field enhancement can be improved in the entire process of the surface-enhanced Raman scattering. That is, the period P1 and the incident angle θ are set so that the two resonance peak wavelength bands BW1 and BW2 include the wavelengths λ1 and λ2. Thus, the degree of electric field enhancement at the excitation wavelength $\lambda 1$ and the degree of electric field enhancement at the Raman scattering wavelength $\lambda 2$ can be improved.

Further, according to the embodiment, the positions of the two resonant peaks and the interval can be adjusted to arbitrary values by suitably changing the raw material of the metal grating, the sectional shape, the period P1, the height H1, and the light incident angle θ. Thus, the wavelength λ in of the light emitted when a target is specified can be suitably selected, and the width of the measurement wavelength range can be widened.

Further, in the embodiment, the Raman scattering wavelength $\lambda 2$ has a wavelength ($\lambda 2 > \lambda 1$) longer than the excitation wavelength $\lambda 1$.

By doing this, between a Stokes component and an anti-Stokes component of Raman scattering light, the Stokes component having a higher scattering intensity can be measured. Incidentally, in this embodiment, the anti-Stokes component of $\lambda 2 < \lambda 1$ may be used.

Further, in this embodiment, as shown in FIG. 7, the linearly polarized light in which a component (orthogonal projection of the polarization direction to the plane of the base member 100) of the polarization direction parallel to the plane of the base member 100 is parallel to the arrangement direction D1 of the first projection group 110 is incident as the incident light.

By doing this, the compression wave of free electron plasma is induced in the direction along the direction D1 by the linearly polarized light, and the surface plasmon propagating along the arrangement direction D1 of the first projection group 110 can be excited.

Further, in this embodiment, as described later in FIG. 12, a second projection group 200 made of a metal may be provided on a top surface 220 of the first projection group 110. The second projection group 200 may be arranged at a second period P2 (P2<P1) shorter than the first period P1 along the direction D1 parallel to the plane of the base member 100.

Further, in this embodiment, as described later in FIG. 12, a third projection group 210 made of a metal may be provided on a surface 230 on which the first projection group 110 is arranged and which is located between adjacent projections of the first projection group 110 (the bottom 230 between the adjacent projections of the first projection group 110). The third projection group 210 may be arranged at a third period P3 (P3<P1) shorter than the first period P1 along the direction D1 parallel to the plane of the base member 100.

By doing this, propagating surface plasmon is excited by the first projection group 110, and localized surface plasmon is excited in the second projection group 200 and the third projection group 210 by the propagating surface plasmon. As a result, the degree of electric field enhancement at the excitation wavelength and at the Raman scattering wavelength can be further improved.

5. Modified Example

Figure 10:
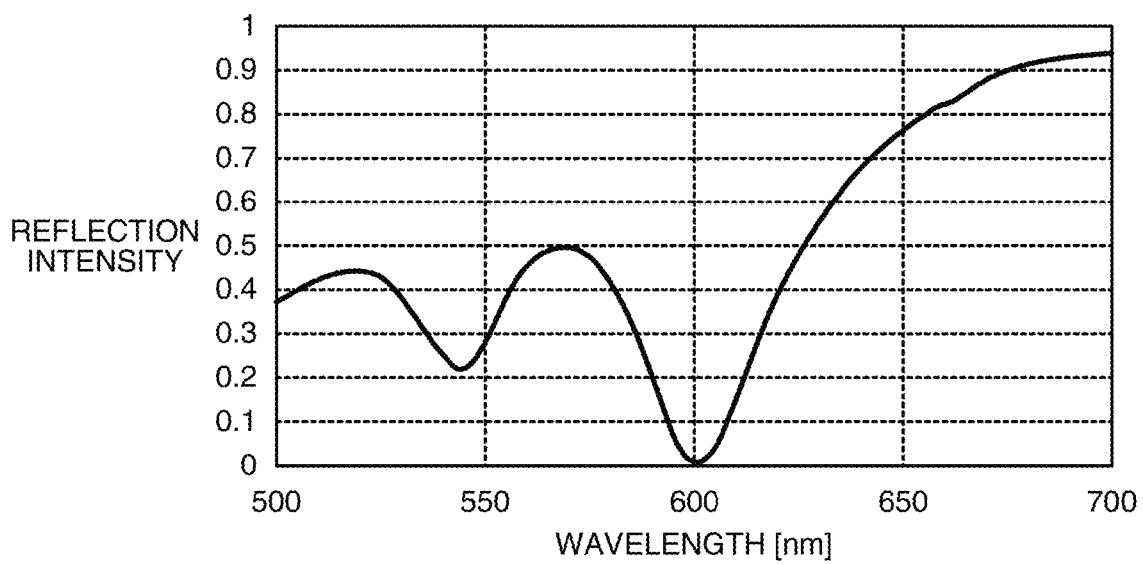
FIG. 10 is a view of a characteristic example of reflected light intensity of a sensor chip of a modified example.

In FIG. 8, although a description has been made of a case where the metal grating 150 is made of Ag, in this embodiment, the metal grating 150 may be made of Au. FIG. 10 shows a characteristic example of reflected light intensity of a sensor chip in this case. FIG. 10 shows the characteristic example in the case where the light incident angle θ with respect to the metal grating is 5 degrees, the light polarization direction is perpendicular to the groove of the metal grating, the section of the projection is rectangular (approximately rectangular), the period P1 is 500 nm, and the height H1 is 40 nm.

As shown in FIG. 10, one of two resonant peaks is located at a wavelength of 545 nm, and the other is located at a wavelength of 600 nm. The two resonant peaks are adjusted to be approximately equal to the excitation wavelength and the Raman scattering wavelength, so that a high surface-enhanced Raman scattering signal can be acquired.

In the metal grating made of Au, as compared with the metal grating made of Ag shown in FIG. 8, the wavelengths of the two resonant peaks are different, the resonant peak is rather broad, and the resonant peak is shallow. However, as compared with the case where only one resonant peak is used, the effect of enhancing the surface-enhanced Raman scattering signal is significantly improved. Further, surface deterioration due to oxidation or sulfuration can be suppressed by using Au. Incidentally, as shown in FIG. 8, when Ag is used, as compared with Au, the resonant peak is narrow and deep. Thus, as compared with Au, the enhancing effect of the surface-enhanced Raman scattering signal can be further improved.

Here, in the embodiment, although Ag or Au is used which has physical properties to strongly generate the surface plasmon, the surface plasmon polariton and the surface-enhanced Raman scattering, in the embodiment, a metal such as Pt (platinum), Cu (copper) or Al (aluminum) may be used.

6. Second Structural Example

In the above embodiment, although the propagating surface plasmon is excited by the first projection group 110, in this embodiment, a diffraction grating may include another projection group (fine metal structure) to excite localized surface plasmon. A second structural example of such a sensor chip will be described with reference to FIG. 11 and FIG. 12.

Figure 11:
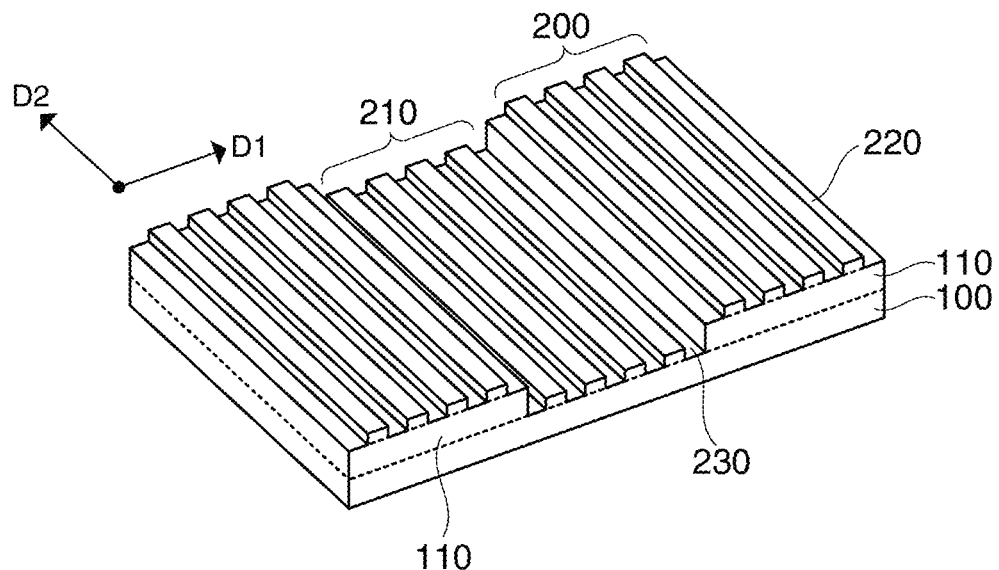
FIG. 11 is a perspective view of a second structural example of a sensor chip.

FIG. 11 is a perspective view of the second structural example of the sensor chip. The sensor chip includes a base member 100, a first projection group 110, a second projection group 200 and a third projection group 210. Incidentally, in the following, the same components as in FIG. 7 are denoted by the same reference numeral, and an explanation is suitably omitted.

As shown in FIG. 11, the first projection group 110 is periodically arranged along the first direction D1 parallel to the plane of the base member 100. The second projection group 200 is periodically arranged along the direction D1 on a top surface 220 of the first projection group 110. The third projection group 210 is periodically arranged along the direction D1 on a bottom surface 230 (plane of the base member 100) between projections of the first projection group 110.

More specifically, in each projection of the second projection group 200 and the third projection group 210, the sectional shape of the projection in the arrangement direction D1 is formed into a convex shape from the top surface 220 or the bottom surface 230. The convex shape is a rectangle, a trapezoid, an arc, or the like. For example, as shown in FIG. 11, the second projection group 200 and the third projection group 210 are formed into a stripe shape parallel to the direction D2 when the base member 100 is seen in a plan view. The second projection group 200 and the third projection group 210 may be made of the same material as the first projection group 110, or may be made of a different material (conductive or semiconductive).

Figure 12:
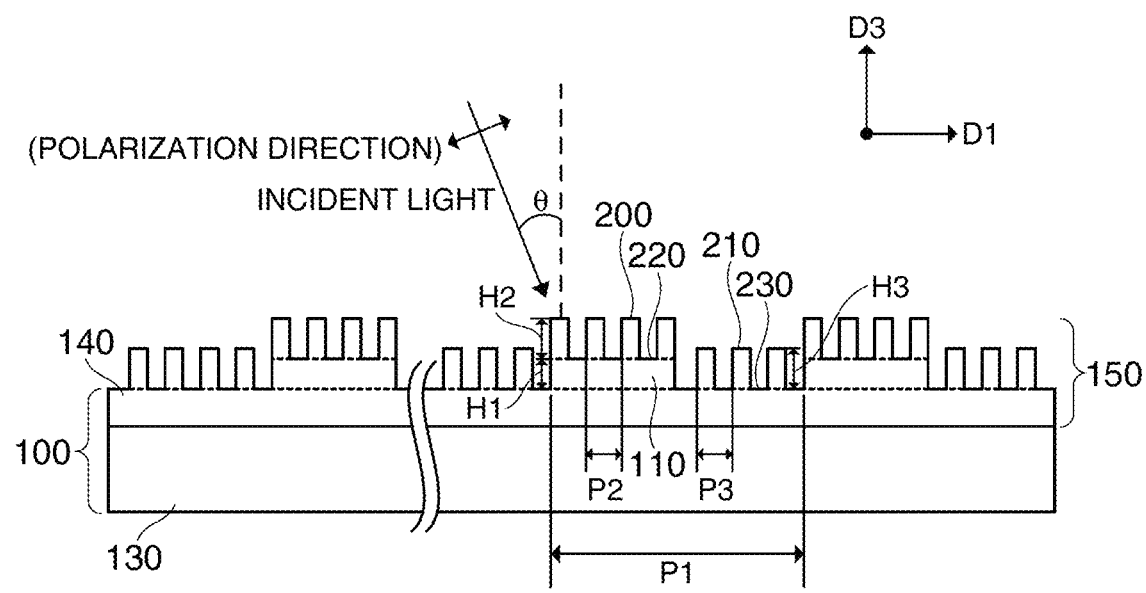
FIG. 12 is a sectional view of the second structural example of the sensor chip.

FIG. 12 is a sectional view of the sensor chip of the second structural example. The section of the sectional view is a surface perpendicular to the plane of the base member 100, and is a surface parallel to the direction D1. As shown in FIG. 12, the second projection group 200 has a height H2 from the top surface 220, and is arranged at a period P2 shorter than P1. The third projection group 210 has a height H3 from the bottom surface 230, and is arranged at a period P3 shorter than P1. For example, it is preferable that the period P2 and P3 are set to be 500 nm or less, and the height H2 and H3 are set to be 200 nm or less. Incidentally, the height H3 may be H3>H1, or may be H3≤H1.

Here, in the above, although the arrangement directions of the second projection group 200 and the third projection group 210 are the same arrangement direction D1 as the first projection group 110, in this embodiment, the arrangement directions of the second projection group 200 and the third projection group 210 may be different from D1. In this case, the arrangement periods P2 and P3 are arrangement periods in the direction D1.

Next, the surface-enhanced Raman scattering by the sensor chip of the second structural example will be described. In this embodiment, the excitation light is inclined by an angle θ and is incident on the sensor chip. Then, as described above, the propagating surface plasmon having two resonant peaks at the excitation wavelength (Rayleigh scattering wavelength) and Raman scattering wavelength is excited by the first projection group 110. The surface plasmon propagates along the surface of the metal grating 150, and excites localized surface plasmon in the second projection group 200 and the third projection group 210. The localized surface plasmon excites enhanced electric field between the projections of the second projection group 200 and the third projection group 210, and surface-enhanced Raman scattering is generated by the interaction between the enhanced electric field and a target. At this time, since the projection interval of the second projection group 200 and the third projection group 210 is narrow, the intense enhanced electric field is excited between the projections. Thus, even when one to several targets are adsorbed between the projections, the intense surface-enhanced Raman scattering can be generated by the enhanced electric field.

7. Analyzing Apparatus

Figure 13:
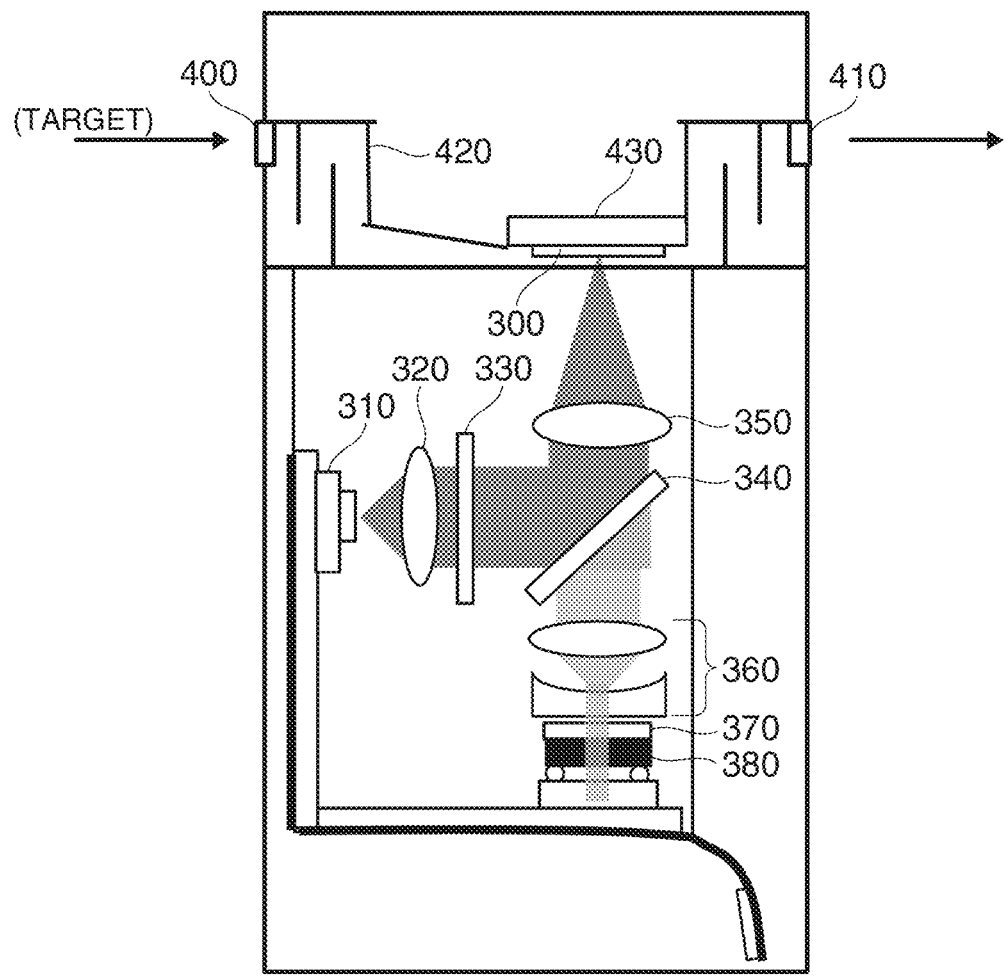
FIG. 13 is a view of a structural example of an analyzing apparatus.

FIG. 13 shows a structural example of an analyzing apparatus including the sensor chip of the embodiment. The analyzing apparatus (spectral apparatus in a broad sense) includes a sensor chip 300 (optical device), a light source 310, a collimator lens 320, a polarization control element 330, an objective lens 350 (first optical system), a dichroic mirror 340, a condenser lens 360, an etalon 370 (340, 360 and 370 denote a second optical system in a broad sense), an optical detector 380 (detector) and a conveyance part 420. Incidentally, the analyzing apparatus of the embodiment is not limited to the structure of FIG. 13, and various modifications can be made, for example, some (for example, the conveyance part) of the components are omitted, or another component is added.

The light source 310 emits a laser light to excite surface plasmon polariton and surface-enhanced Raman scattering. The laser light emitted from the light source 310 is made parallel by the collimator lens 320, and is made linearly polarized by the polarization control element 330. The laser light passing through the polarization control element 330 is guided to the sensor chip 300 by the dichroic mirror 340, is concentrated by the objective lens 350, and is incident on the sensor chip 300. For example, a metal grating or a detection material selecting mechanism is formed on the surface of the sensor chip 300. The period of the metal grating is shorter than the wavelength of the laser light.

An arrow shown in FIG. 13 indicates a conveyance direction of a target. The target is introduced from a carry-in port 400 into the inside of the conveyance part 420 by controlling driving of a fan (not shown), and is discharged from a discharge port 410 to the outside of the conveyance part 420. At this time, a part of the target passing through the conveyance part 420 is attached to the sensor chip 300 supported by a support part 430, and the target (not shown) is arranged on the surface of the sensor chip 300.

When the laser light is incident on the metal grating surface, free electrons resonate and oscillate by the oscillation of the laser light, and a very highly enhanced electric field is generated through the surface plasmon polariton in the vicinity of the metal grating surface. For example, when one to several target materials enter the enhanced electric field, surface-enhanced Raman scattering is generated therefrom. Rayleigh scattering light and Raman scattering light from the sensor chip 300 pass through the objective lens 350, and are guided to the optical detector 380 by the dichroic mirror 340. The scattering light is concentrated by the condenser lens 360, passes through the etalon 370 (spectroscope), and is incident on the light detector 380. The Raman scattering light is spectrally separated from the scattering light by the etalon 370, and the Raman scattering light is received by the optical detector 380. In this way, the scattering light is spectrally decomposed, and spectrum information of the target is obtained.

According to the analyzing apparatus, since the sensor chip 300 is provided, the surface-enhanced Raman scattering is generated, the Raman scattering light is selectively spectrally separated, and the target can be detected. As a result, the sensor sensitivity is improved, and the target can be specified from the surface-enhanced Raman scattering spectrum.

Incidentally, the analyzing apparatus of the embodiment can be widely applied to a sensing apparatus used for detection of drug or explosive material, medical or health diagnosis, and detection of food. Further, the analyzing apparatus can be used as an affinity sensor to detect the presence or absence of adsorption of a material, such as the presence or absence of adsorption of antigen in antigen-antibody reaction.

Figure 14:
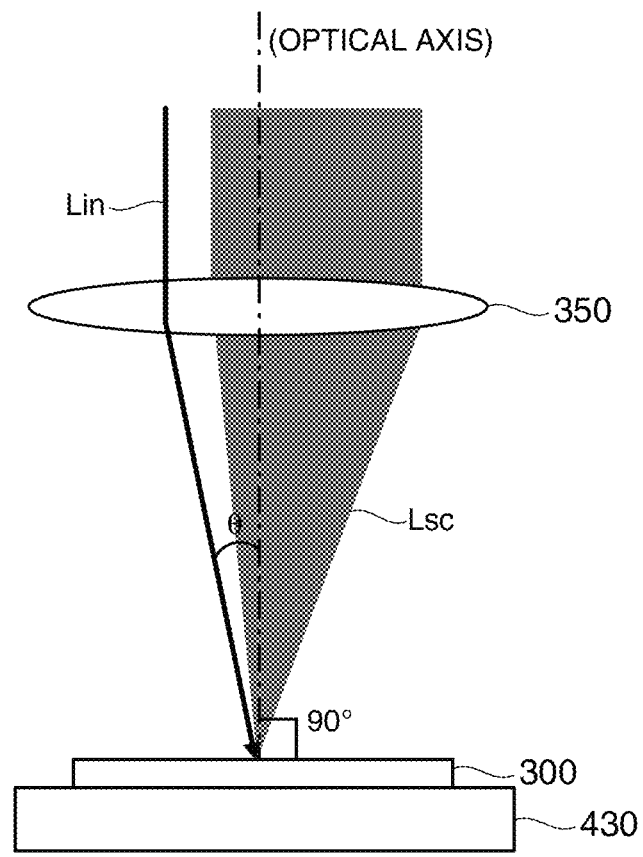
FIG. 14 is an explanatory view of a first method for causing incident light to be inclined and to be incident.

FIG. 14 is an explanatory view of a first method for causing incident light to be inclined and to be incident on a sensor chip. In the first method, the incident beam Lin (incident light) is deviated from the optical axis of an objective lens 350 and is made incident, so that the incident beam Lin is inclined with respect to the sensor chip 300.

Specifically, the sensor chip 300 is arranged on a support part 430 vertically to the optical axis of the objective lens 350. Then, the incident beam Lin is separated from the optical axis of the objective lens 350 by a specified distance and is incident in parallel to the optical axis of the objective lens 350. The specified distance is the distance by which the incident angle of the incident beam Lin to the sensor chip 300 becomes θ by refraction of the objective lens 350. A scattering light Lsc (or reflected light) from the sensor chip 300 is incident on the objective lens 350, and is guided to a next stage optical system such as the dichroic mirror 340 by the objective lens 350.

Figure 15:
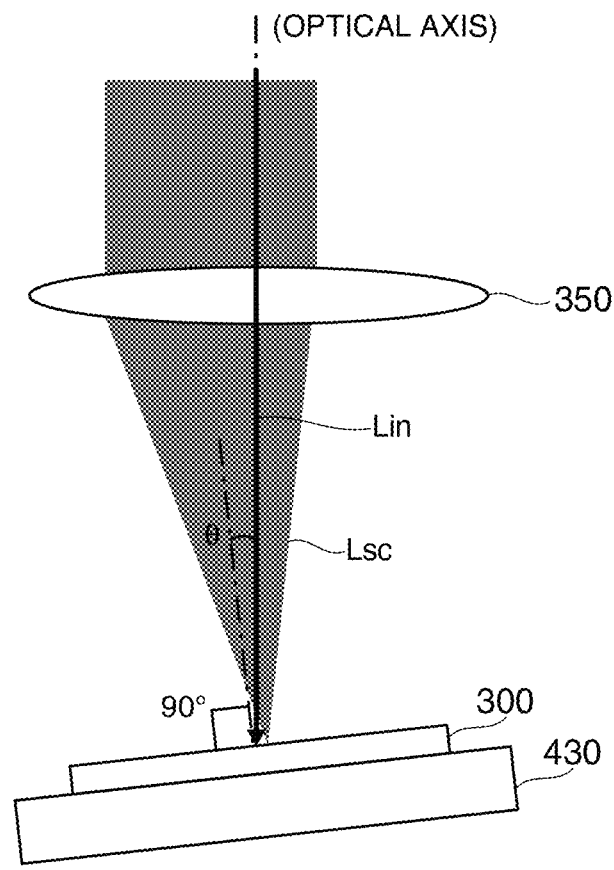
FIG. 15 is an explanatory view of a second method for causing incident light to be inclined and to be incident.

FIG. 15 is an explanatory view of a second method for causing incident light to be inclined and to be incident on a sensor chip. In this second method, an incident beam Lin (incident light) is made to coincide with the optical axis of an objective lens 350 and is made incident, while a sensor chip 300 is arranged to be inclined with respect to the optical axis of the objective lens 350, so that the incident beam Lin is inclined with respect to the sensor chip 300.

Specifically, an angle between a normal line of the plane (plane of the base member 100) of the sensor chip 300 and the optical axis of the objective lens 350 is arranged to be θ. The incident beam Lin is made incident along the optical axis of the objective lens 350. Then, the incident beam Lin is not refracted by the objective lens 350, and is incident on the sensor chip 300 at an incident angle θ. A scattering light Lsc from the sensor chip 300 is guided to a next optical system by the objective lens 350 similarly to the first method. Incidentally, in this embodiment, in order to incline the sensor chip 300, as shown in FIG. 15, a support part 430 may be inclined, or a support surface of the support part 430 may be made an inclined surface.

Although the embodiments have been described in detail, it would be easily understood for a person skilled in the art that many modifications can be made without departing from the novel features and the effects of the invention. Accordingly, all such modifications are included within the scope of the invention. For example, in the specification and the drawings, a term (target material, excitation light, metal grating, metal, etc.) described together with a comprehensive or synonymous different term (target, incident light, diffraction grating, conductor, etc.) at least once can be replaced by the different term in any portion of the specification or the drawings. Further, the structure and operation of the optical device, the analyzing apparatus and the like are not limited to those described in the embodiments, and various modifications can be made thereto.

What is claimed is:

1. An optical device comprising:
a first projection group in which electrically conductive projections are arranged at a first period along a direction parallel to a virtual plane, wherein
the first projection group is configured such that when light traveling in an incident direction inclined with respect to a vertical line directed to the virtual plane is incident on the first projection group, surface plasmon resonance is generated at a first resonance peak wavelength and a second resonance peak wavelength,
a first resonance peak wavelength band including the first resonance peak wavelength includes an excitation wavelength $\lambda 1$ in surface-enhanced Raman scattering,
a second resonance peak wavelength band including the second resonance peak wavelength includes a Raman scattering wavelength $\lambda 2$ in the surface-enhanced Raman scattering, and
when an excitation frequency of the excitation wavelength $\lambda 1$ is k1, a Raman frequency of the Raman scattering wavelength $\lambda 2$ is k2, a dispersion curve of a surface plasmon polariton generated by the surface plasmon resonance is f(k), a light frequency of the incident h is ki, the first period is P1, and an incident angle between the incident direction and the vertical line is θ, the following relations are satisfied:

$f(k1)=2\pi/P1+ki\times\sin\theta$, and $f(k2)=2\pi/P1-ki\times\sin\theta$.

2. The optical device according to claim 1, wherein the Raman scattering wavelength $\lambda 2$ is longer than the excitation wavelength $\lambda 1$.

3. The optical device according to claim 1, wherein the incident light is a linearly polarized light in which a component of a polarization direction parallel to the virtual plane is parallel to an arrangement direction of the first projection group.

4. The optical device according to claim 1, wherein
a second projection group of electric conductors is provided on a top surface of the first projection group, and
the second projection group is arranged at a second period that is shorter than the first period along the direction parallel to the virtual plane.

5. The optical device according to claim 1, wherein
a third projection group of electric conductors is provided on a surface on which the first projection group is arranged and which is located between adjacent projections of the first projection group, and
the third projection group is arranged at a third period that is shorter than the first period along the direction parallel to the virtual plane.

6. An analyzing apparatus comprising:
a light source;
an optical device according to claim 1;
a first optical system that causes incident light of the wavelength $\lambda 1$ from the light source to be inclined with respect to the vertical line directed to the virtual plane of the optical device and causes the light to be incident on the electrically conductive projections;
a second optical system that extracts Raman scattering light from the light scattered or reflected by the electrically conductive projections of the optical device; and
a detector to detect the Raman scattering light received through the second optical system.

7. An analyzing apparatus comprising:
a light source;
an optical device according to claim 2;
a first optical system that causes incident light of the wavelength $\lambda 1$ from the light source to be inclined with respect to the vertical line directed to the virtual plane of the optical device and causes the light to be incident on the electrically conductive projections;
a second optical system that extracts Raman scattering light from the light scattered or reflected by the electrically conductive projections of the optical device; and
a detector to detect the Raman scattering light received through the second optical system.

8. An analyzing apparatus comprising:
a light source;
an optical device according to claim 3;
a first optical system that causes incident light of the wavelength $\lambda 1$ from the light source to be inclined with respect to the vertical line directed to the virtual plane of the optical device and causes the light to be incident on the electrically conductive projections;
a second optical system that extracts Raman scattering light from the light scattered or reflected by the electrically conductive projections of the optical device; and
a detector to detect the Raman scattering light received through the second optical system.

9. An analyzing apparatus comprising:
a light source;
an optical device according to claim 4;
a first optical system that causes incident light of the wavelength $\lambda 1$ from the light source to be inclined with respect to the vertical line directed to the virtual plane of the optical device and causes the light to be incident on the first and second projection groups;
a second optical system that extracts Raman scattering light from the light scattered or reflected by the optical device; and
a detector to detect the Raman scattering light received through the second optical system.

10. An analyzing apparatus comprising:
a light source;
an optical device according to claim 5;
a first optical system that causes incident light of the wavelength λ1 from the light source to be inclined with respect to the vertical line directed to the virtual plane of the optical device and causes the light to be incident on the first and third projection groups;
a second optical system that extracts Raman scattering light from the light scattered or reflected by the optical device; and
a detector to detect the Raman scattering light received through the second optical system.

11. The analyzing apparatus according to claim 6, wherein the first optical system shifts the incident light from an optical axis of the first optical system and causes the light to be incident, and the light is inclined with respect to the vertical line directed to the virtual plane and is incident on the electrically conductive projections.

12. The analyzing apparatus according to claim 7, wherein the first optical system shifts the incident light from an optical axis of the first optical system and causes the light to be incident, and the light is inclined with respect to the vertical line directed to the virtual plane and is incident on the electrically conductive projections.

13. The analyzing apparatus according to claim 8, wherein the first optical system shifts the incident light from an optical axis of the first optical system and causes the light to be incident, and the light is inclined with respect to the vertical line directed to the virtual plane and is incident on the electrically conductive projections.

14. The analyzing apparatus according to claim 9, wherein the first optical system shifts the incident light from an optical axis of the first optical system and causes the light to be incident, and the light is inclined with respect to the vertical line directed to the virtual plane and is incident on the first and second projection groups.

15. The analyzing apparatus according to claim 6, further comprising a support part that causes the vertical line directed to the virtual plane of the optical device to be inclined with respect to an optical axis of the first optical system, and supports the optical device, wherein
the first optical system causes the incident light to coincide with the optical axis of the first optical system and to be incident, and the incident light is inclined with respect to the vertical line directed to the virtual plane and is incident on the electrically conductive projections.

16. The analyzing apparatus according to claim 7, further comprising a support part that causes the vertical line directed to the virtual plane of the optical device to be inclined with respect to an optical axis of the first optical system, and supports the optical device, wherein
the first optical system causes the incident light to coincide with the optical axis of the first optical system and to be incident, and the incident light is inclined with respect to the vertical line directed to the virtual plane and is incident on the electrically conductive projections.

17. The analyzing apparatus according to claim 8, further comprising a support part that causes the vertical line directed to the virtual plane of the optical device to be inclined with respect to an optical axis of the first optical system, and supports the optical device, wherein
the first optical system causes the incident light to coincide with the optical axis of the first optical system and to be incident, and the incident light is inclined with respect to the vertical line directed to the virtual plane and is incident on the electrically conductive projections.

18. The analyzing apparatus according to claim 9, further comprising a support part that causes the vertical line directed to the virtual plane of the optical device to be inclined with respect to an optical axis of the first optical system, and supports the optical device, wherein
the first optical system causes the incident light to coincide with the optical axis of the first optical system and to be incident, and the incident light is inclined with respect to the vertical line directed to the virtual plane and is incident on the first and second projection groups.

19. A spectroscopic method comprising:
providing a first projection group in which electrically conductive projections are arranged at a first period along a direction parallel to a virtual plane;
causing light traveling in an incident direction inclined with respect to a vertical line directed to the virtual plane to be incident on the first projection group;
generating surface plasmon resonance at a first resonance peak wavelength and a second resonance peak wavelength;
causing a first resonance peak wavelength band including the first resonance peak wavelength to include an excitation wavelength λ1 in surface-enhanced Raman scattering; and
causing a second resonance peak wavelength band including the second resonance peak wavelength to include a Raman scattering wavelength λ2 in the surface-enhanced Raman scattering, wherein
when an excitation frequency of the excitation wavelength λ1 is k1, a Raman frequency of the Raman scattering wavelength λ2 is k2, a dispersion curve of a surface plasmon polariton generated by the surface plasmon resonance is f(k), a light frequency of the incident light is ki, the first period is P1, and an incident anile between the incident direction and the vertical line is θ, the following relations are satisfied:

$$f(k1) = 2\pi/P1 + ki \times \sin\theta, \text{ and}$$

$$f(k2) = 2\pi/P1 - ki \times \sin\theta.$$

* * * * *